(12) United States Patent
Cohen et al.

(10) Patent No.: US 7,659,815 B2
(45) Date of Patent: Feb. 9, 2010

(54) PROCESS FOR PRODUCING AND CONTROLLING THE PACKAGE QUALITY OF ABSORBENT ARTICLES CONTAINING A WETNESS SENSING SYSTEM

(75) Inventors: Jason C. Cohen, Appleton, WI (US); Darold D. Tippey, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 625 days.

(21) Appl. No.: 11/513,832

(22) Filed: Aug. 31, 2006

(65) Prior Publication Data

US 2008/0058743 A1    Mar. 6, 2008

(51) Int. Cl.
*G08B 21/00*    (2006.01)

(52) U.S. Cl. ..................................... 340/540

(58) Field of Classification Search .................. 340/540, 340/604, 602, 573.5, 518
See application file for complete search history.

(56) References Cited

U.S. PATENT DOCUMENTS

| | | | |
|---|---|---|---|
| 4,100,324 A | | 7/1978 | Anderson et al. |
| 4,484,066 A | | 11/1984 | DeBlieux et al. |
| 4,653,491 A | * | 3/1987 | Okada et al. ................. 128/886 |
| 4,768,209 A | | 8/1988 | Yu |
| 5,041,721 A | | 8/1991 | Smith et al. |
| 5,187,723 A | | 2/1993 | Mueller-Stuercken |
| 5,266,928 A | * | 11/1993 | Johnson ....................... 340/604 |
| 5,284,703 A | | 2/1994 | Everhart et al. |
| 5,350,624 A | | 9/1994 | Georger et al. |
| 5,637,165 A | | 6/1997 | Chen |
| 5,838,240 A | * | 11/1998 | Johnson ....................... 340/604 |
| 6,222,450 B1 | * | 4/2001 | Clements ................. 340/568.1 |
| 6,352,497 B1 | | 3/2002 | Hensley et al. |
| 6,354,984 B1 | | 3/2002 | Hensley et al. |
| 6,724,305 B2 | * | 4/2004 | Edwards et al. ........... 340/568.1 |
| 2003/0113529 A1 | | 6/2003 | Gibson et al. |
| 2004/0078014 A1 | | 4/2004 | Shapira |
| 2004/0113801 A1 | | 6/2004 | Gustafson et al. |
| 2005/0196580 A1 | | 9/2005 | Provost et al. |

FOREIGN PATENT DOCUMENTS

| | | |
|---|---|---|
| WO | WO 9200534 | 1/1992 |
| WO | WO 0059429 | 10/2000 |
| WO | WO 0226587 A2 | 4/2002 |
| WO | WO 2004060783 | 7/2004 |

OTHER PUBLICATIONS

PCT International Search Report for PCT/IB2007/052816, dated Feb. 1, 2008.

* cited by examiner

*Primary Examiner*—Phung Nguyen
(74) *Attorney, Agent, or Firm*—Dority & Manning, P.A.

(57) ABSTRACT

The present disclosure is generally directed to process for controlling the quality of absorbent articles containing wetness sensing systems. The wetness sensing system incorporated in the article can include, for instance, metallic conductive leads or other metallic material. A metal sensor can be used in order to ensure that a proper amount of metallic material is contained within the absorbent article thereby confirming the presence of the wetness sensing system. The process of the present disclosure can be carried out at various locations. For instance, the process can be carried out while the articles are being manufactured, after the articles are packaged or during use of the articles. In one embodiment, the process can be carried out at a wholesale or retail location prior to accepting the articles into inventory.

25 Claims, 7 Drawing Sheets

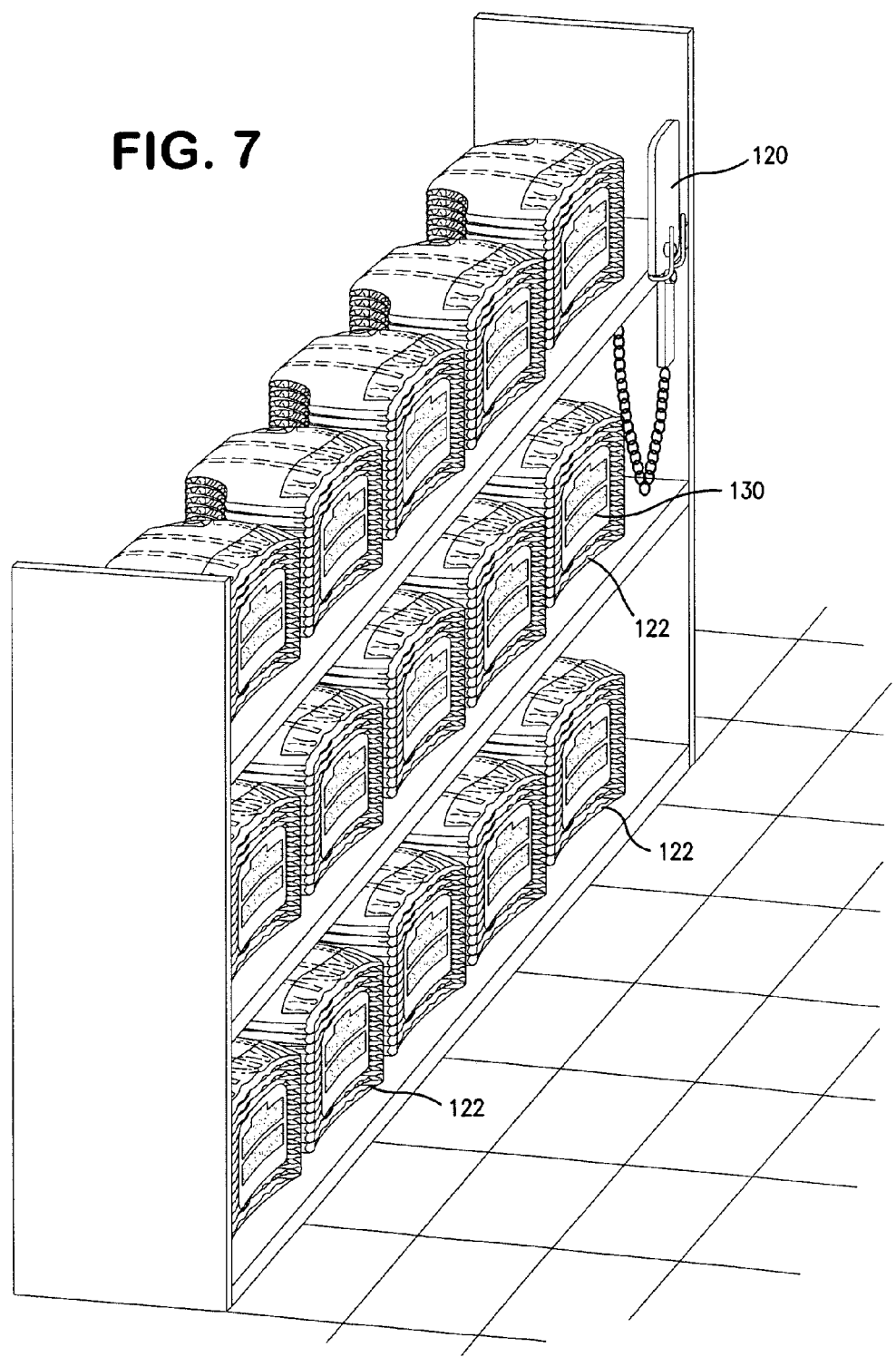

PROCESS FOR PRODUCING AND CONTROLLING THE PACKAGE QUALITY OF ABSORBENT ARTICLES CONTAINING A WETNESS SENSING SYSTEM

BACKGROUND OF THE INVENTION

Absorbent articles such as diapers, training pants, incontinence products, feminine hygiene products, swim undergarments, and the like conventionally include a liquid permeable body-side liner, a liquid impermeable outer cover, and an absorbent core. The absorbent core is typically located in between the outer cover and the liner for taking in and retaining liquids (e.g., urine) exuded by the wearer.

The absorbent core can be made of, for instance, super absorbent particles. Many absorbent particles, especially those sold under the tradename HUGGIES™ by the Kimberly-Clark Corporation, are so efficient at absorbing liquids that it is sometimes difficult to tell whether or not the absorbent article has been insulted with a body fluid.

Accordingly, various types of moisture or wetness indicators have been suggested for use in absorbent articles. The wetness indicators may include alarm devices that are designed to assist parents or attendants identify a wet diaper condition early on. The devices produce either a visual or an audible signal.

In some embodiments, for instance, conductive threads or foils have been placed in the absorbent articles in the machine direction. The conductive materials serve as conductive leads for a signaling device and form an open circuit in the article that can be closed when a body fluid, such as urine, closes the circuit. Incorporating a wetness sensing system into an absorbent article during its manufacture, however, can be problematic. For instance, many absorbent articles are made at relatively high speeds. At such speeds it can be difficult to not only incorporate a wetness sensing system into the absorbent article, but to ensure that the conductive leads are positioned properly. Thus, a need currently exists for a quality control process that can be used to verify that the absorbent articles contain a desired component or item, such as the metallic conductive leads of a wetness sensing system.

SUMMARY OF THE INVENTION

In general, the present disclosure is directed to a process for producing and controlling the quality of manufactured absorbent articles incorporating a wetness sensing system. As will be described below, a metal sensor may be used in order to detect the presence of a wetness sensing system in one or more absorbent articles in order to ensure that the articles have been manufactured with the desired qualities and functions. Metal detectors are currently used by many manufacturers to confirm that no foreign metal objects have accidentally been placed into any product packages. In the present disclosure, however, a metal sensor is used in order to ensure that a proper amount of metallic material is present in the product. The sensitivity of the metal detector can be varied depending on the particular application. For instance, in one embodiment, the metal detector may be simply used to indicate that a metallic material is present or absent. In a perhaps a more sophisticated process, alternatively, a metal sensor may be used in order to sense a specific amount of metallic material present within a product or within a package of products.

For example, in one embodiment, the present disclosure is directed to a process for producing and controlling the package quality of manufactured absorbent articles. The process includes the steps of incorporating into an absorbent article a wetness sensing system that is configured to detect the presence of a substance such as urine and/or fecal matter. The wetness sensing system can comprise at least one metallic conductive element.

In accordance of the present disclosure, the absorbent article is passed in proximity to a metal sensor. The metal sensor detects the presence of the wetness sensing system in order to confirm that the wetness sensing system has been properly incorporated into the article. The above process can be carried out as the absorbent article is being made, after the absorbent article has been packaged, or even during use of the absorbent article.

In one embodiment, for instance, the process can include the step of packaging together a plurality of absorbent articles each incorporating a wetness sensing system. The package is then passed in proximity to the metal sensor wherein the metal sensor can be configured to indicate that each absorbent article in the package contains the wetness sensing system. For instance, the metal sensor may be configured to detect whether the package contains sufficient amount of a metallic material that confirms that each absorbent article in the package contains the wetness sensing system.

In one embodiment, for instance, the metal sensor may be configured to generate a signal when a package of the absorbent articles contains a metallic material in an amount outside of a pre-selected range, thus indicating that the package contains more or less metallic material than desired. This signal, for instance, can be audible, can be visual, or can be a combination of audible and visual signals. The signal can also be communicated to a product inspection system to accept or reject product on line and track the results of product manufactured to specifications verses out of specification product. This SIGNAL can be electronically communicated to the product main line to alert the operators in real time they are producing out of specification product.

The amount of metallic material that may be present in the absorbent articles can vary dramatically depending upon the particular application and the manner in which the articles are constructed. For exemplary purposes only, for instance, in one embodiment each article can contain from about 0.05 grams of a metallic material to about 1 gram of a metallic material, such as from about 0.075 grams per article to about 0.7 grams per article. The metallic material can be any suitable material, such as aluminum. Thus, the pre-selected range to which the metal sensor is set can be from about 0.05 grams per absorbent article times the number of absorbent articles in the package to about 1 gram per absorbent article times the number of absorbent articles in the package.

As described above, the process of the present disclosure can be carried out at different times during the manufacture, packaging, sale and use of the absorbent article. For instance, in one embodiment, the absorbent articles can be packaged together and can be passed in proximity to the metal sensor prior to being shipped from the location in which the products are packaged. Alternatively, the packages can be passed in proximity to the metal sensor at a wholesale or retail location as the package is being added to inventory. In still another embodiment, the metal sensor may be available for use by a consumer at the point of sale prior to the consumer purchasing the package.

In general, any suitable metal sensor may be used in the process of the present disclosure depending upon the metallic material contained in the absorbent article. For instance, the metal sensor may comprise an induction balance metal detector that operates at a frequency of from about 30 kHz to about 300 kHz. Alternatively, a pulse induction metal detector may be used. Of particular advantage, most metal detectors can be programmed so as to discriminate between different types of metallic materials and between the amounts of material present in a package. For example, in one embodiment, the wetness sensing system incorporated into the absorbent articles may contain a ferrous material and the metal sensor used to scan the article may be configured to only detect ferrous metals.

In addition to quality control processes, the present disclosure is also directed to a package of absorbent articles. For example, the package of absorbent articles may contain a plurality of absorbent articles wherein at least certain of the articles contain a wetness sensing system that comprises at least one metallic conductive element. The plurality of absorbent articles may be enclosed within a package housing. The package housing can include an interior surface facing the articles and an exterior surface.

In accordance with the present disclosure, graphics can be applied to the exterior surface of the package housing. The graphics can include instructions directed to placing the package into proximity with a metal sensor for confirming the presence of a wetness sensing system in at least certain of the absorbent articles. The absorbent articles, for instance, may comprise a diaper having an outer cover, a bodyside liner and an absorbent structure positioned in between the outer cover and the bodyside liner.

Other features and aspects of the present disclosure are discussed in greater detail below.

BRIEF DESCRIPTION OF THE DRAWINGS

A full and enabling disclosure including the best mode thereof to one skilled in the art is set forth more particularly in the remainder of the specification, including reference to the accompanying figures, in which:

FIG. 7 is a perspective view of another embodiment of a process for detecting the presence of wetness sensing systems within packaged absorbent articles.

Figure 1:
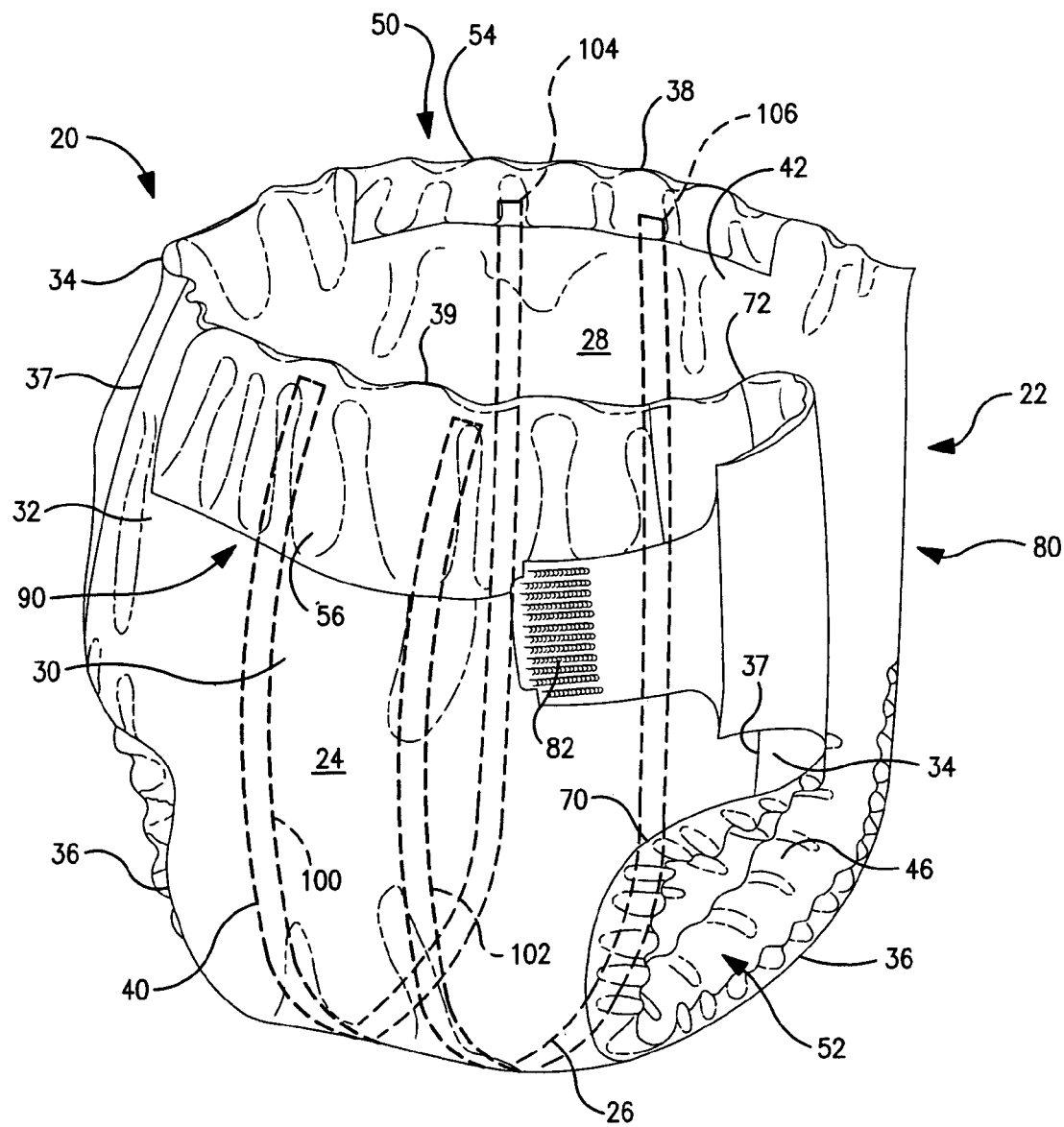
FIG. 1 is a rear perspective view of one embodiment of an absorbent article that may be used in the process of the present disclosure.

Repeat use of reference characters in the present specification and drawings is intended to represent the same or analogous features or elements of the present invention.

DETAILED DESCRIPTION OF THE INVENTION

It is to be understood by one of ordinary skill in the art that the present discussion is a description of exemplary embodiments only, and is not intended as limiting the broader aspects of the present invention.

In general, the present disclosure is directed to a process for producing absorbent articles containing a wetness sensing system. More particularly, the present disclosure is directed to a process for ensuring that the wetness sensing system is present within the articles after they have been produced. The quality control process of the present disclosure can be used by manufacturers to ensure that their products meet specifications, by wholesalers and retailers prior to placing the products in inventory, and even by consumers in order to build consumer confidence in the products.

The wetness sensing system incorporated into the absorbent articles may vary dramatically depending upon particular article being produced and the desired result. Regardless, the wetness sensing system is configured to indicate the presence of a body fluid in the absorbent article or other changes in the condition of the product or wear. The absorbent article may be, for instance, a diaper, a training pant, an incontinence product, a feminine hygiene product, a medical garment, a bandage, or the like. In one embodiment, for instance, the absorbent articles may include an open circuit that becomes closed when a conductive fluid, such as a body fluid, is sensed in between a pair of conductive leads. The conductive leads or other parts of the wetness sensing system can be made from a metallic material. In order to ensure that the wetness sensing system has been incorporated into the article, the article can be placed in proximity to a metal sensor which senses the metallic material within the wetness sensing system.

Figure 2:
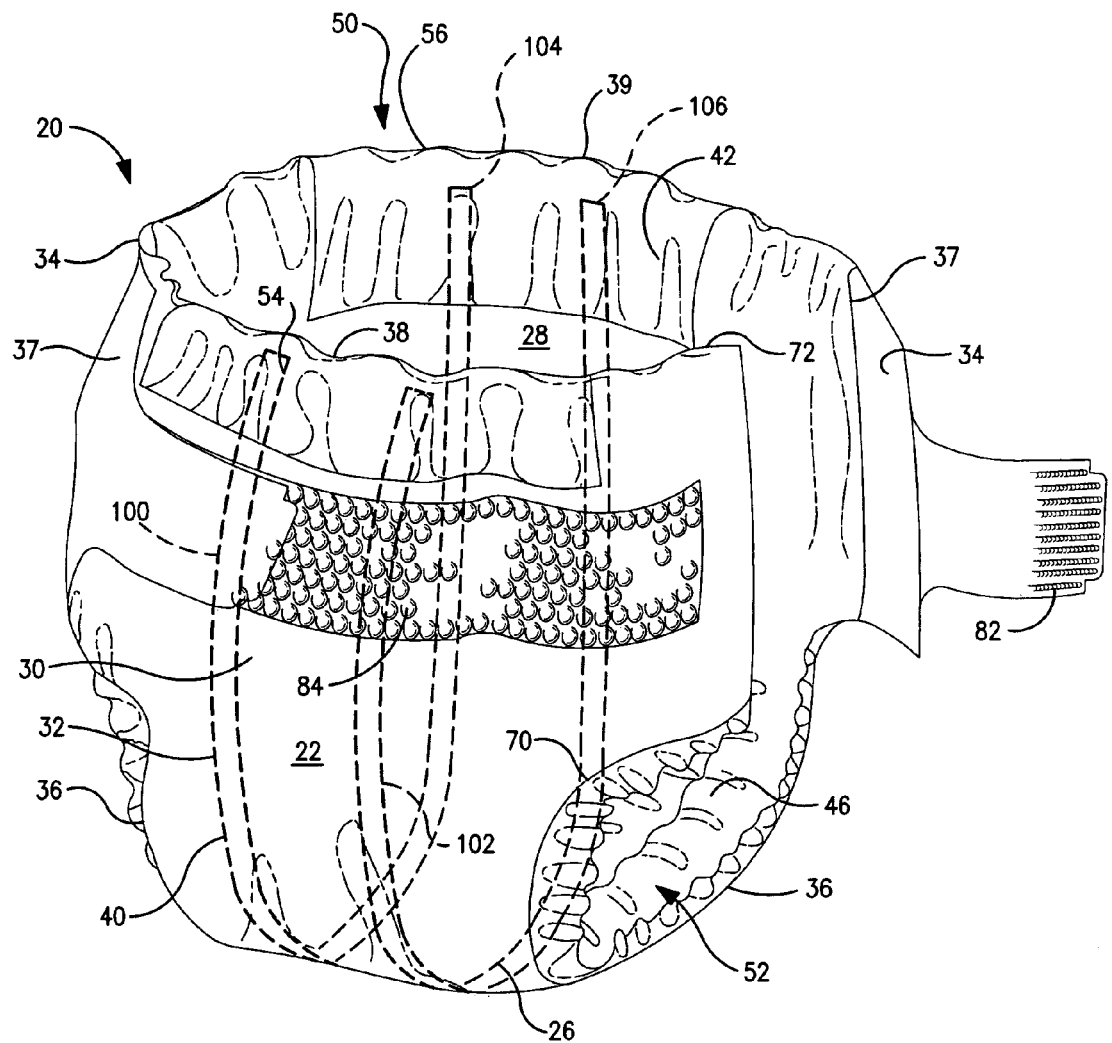
FIG. 2 is a front perspective view of the absorbent article illustrated in FIG. 1.
Figure 3:
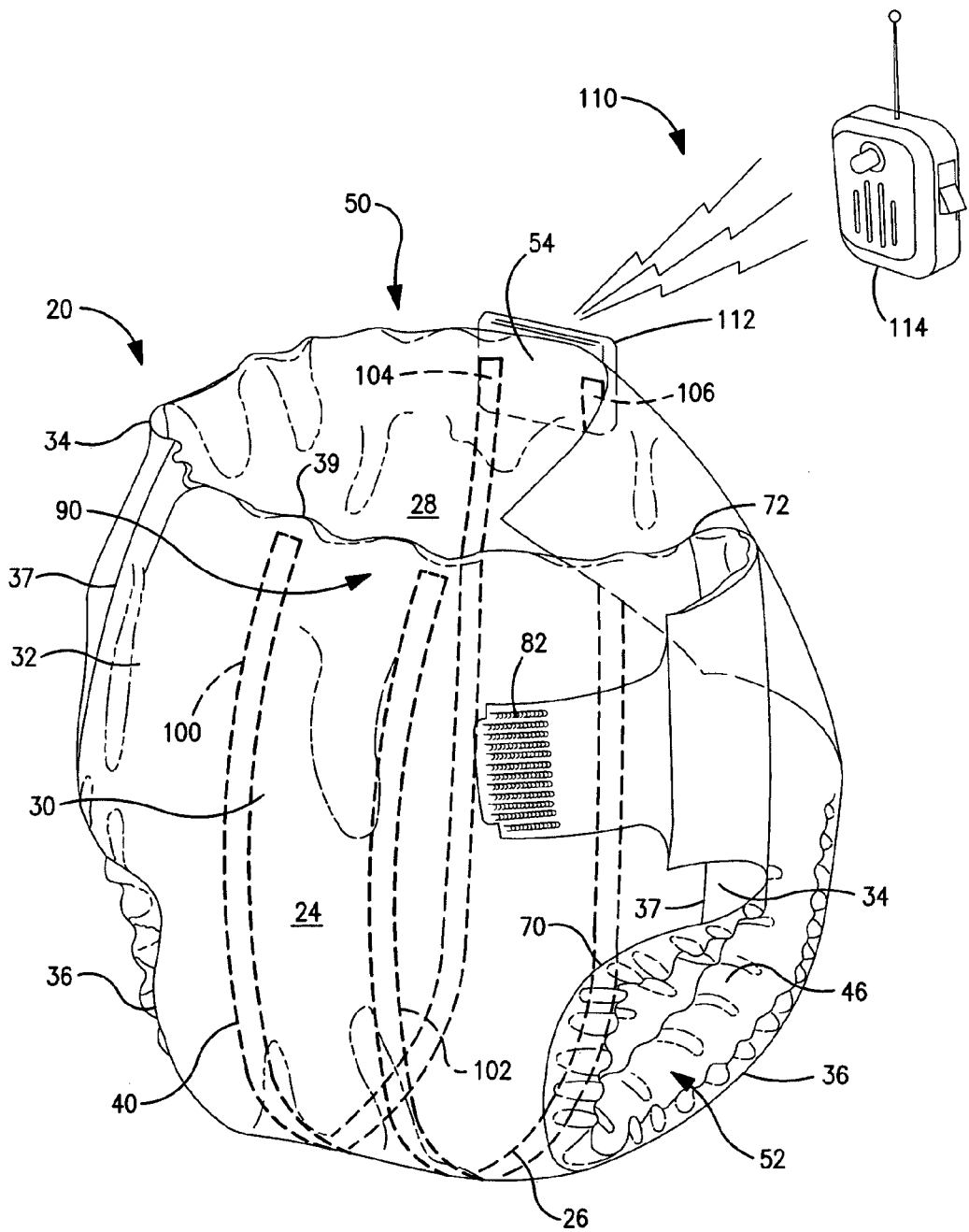
FIG. 3 is a perspective view of the absorbent article illustrated in FIG. 1 further including one embodiment of a signaling device.

Referring to FIGS. 1, 2 and 3, for exemplary purposes only, an absorbent article 20 that may be used in the process of the present disclosure shown. For example, in FIGS. 1 and 3, a diaper 20 is illustrated from the rear of the diaper. In FIG. 2, however, the diaper 20 is shown from the front.

The diaper 20 defines a pair of longitudinal end regions, otherwise referred to herein as a front region 22 and a back region 24, and a center region, otherwise referred to herein as a crotch region 26, extending longitudinally between and interconnecting the front and back regions 22, 24. The diaper 20 also defines an inner surface 28 adapted in use (e.g., positioned relative to the other components of the article 20) to be disposed toward the wearer, and an outer surface 30 opposite the inner surface. The front and back regions 22, 24 are those portions of the diaper 20, which when worn, wholly or partially cover or encircle the waist or mid-lower torso of the wearer. The crotch region 26 generally is that portion of the diaper 20 which, when worn, is positioned between the legs of the wearer and covers the lower torso and crotch of the wearer. The absorbent article 20 has a pair of laterally opposite side edges 36 and a pair of longitudinally opposite waist edges, respectively designated front waist edge 38 and back waist edge 39.

The illustrated diaper 20 includes a chassis 32 that, in this embodiment, encompasses the front region 22, the back region 24, and the crotch region 26. The chassis 32 includes an outer cover 40 and a bodyside liner 42 that may be joined to the outer cover 40 in a superimposed relation therewith by adhesives, ultrasonic bonds, thermal bonds or other conventional techniques. The liner 42 may suitably be joined to the outer cover 40 along the perimeter of the chassis 32 to form a front waist seam and a back waist seam. The liner 42 may suitably be joined to the outer cover 40 to form a pair of side seams in the front region 22 and the back region 24. The liner 42 can be generally adapted, i.e., positioned relative to the other components of the article 20, to be disposed toward the wearer's skin during wear of the absorbent article. The chassis 32 may further include an absorbent structure disposed between the outer cover 40 and the bodyside liner 42 for absorbing liquid body exudates exuded by the wearer, and may further include a pair of containment flaps 46 secured to the bodyside liner 42 for inhibiting the lateral flow of body exudates.

The elasticized containment flaps 46 define a partially unattached edge which assumes an upright configuration in at least the crotch region 26 of the diaper 20 to form a seal against the wearer's body. The containment flaps 46 can extend longitudinally along the entire length of the chassis 32 or may extend only partially along the length of the chassis.

To further enhance containment and/or absorption of body exudates, the diaper 20 may also suitably include leg elastic members, as are known to those skilled in the art. The leg elastic members can be operatively joined to the outer cover 40 and/or the bodyside liner 42 and positioned in the crotch region 26 of the absorbent article 20.

As shown, the absorbent article 20 further includes a pair of opposing elastic side panels 34 that are attached to the back region of the chassis 32. As shown particularly in FIGS. 1 and 2, the side panels 34 may be stretched around the waist and/or hips of a wearer in order to secure the garment in place. The elastic side panels are attached to the chassis along a pair of opposing longitudinal edges 37. The side panels 34 may be attached or bonded to the chassis 32 using any suitable bonding technique. For instance, the side panels 34 may be joined to the chassis by adhesives, ultrasonic bonds, thermal bonds, or other conventional techniques.

In an alternative embodiment, the elastic side panels may also be integrally formed with the chassis 32. For instance, the side panels 34 may comprise an extension of the bodyside liner 42, of the outer cover 40, or of both the bodyside liner 42 and the outer cover 40.

In the embodiments shown in the figures, the side panels 34 are connected to the back region of the absorbent article 20 and extend over the front region of the article when securing the article in place on a user. It should be understood, however, that the side panels 34 may alternatively be connected to the front region of the article 20 and extend over the back region when the article is donned.

With the absorbent article 20 in the fastened position as partially illustrated in FIGS. 1 and 2, the elastic side panels 34 may be connected by a fastening system 80 to define a 3-dimensional diaper configuration having a waist opening 50 and a pair of leg openings 52. The waist opening 50 of the article 20 is defined by the waist edges 38 and 39 which encircle the waist of the wearer.

In the embodiments shown in the figures, the side panels are releasably attachable to the front region 22 of the article 20 by the fastening system. It should be understood, however, that in other embodiments the side panels may be permanently joined to the chassis 32 at each end. The side panels may be permanently bonded together, for instance, when forming a training pant or absorbent swimwear.

The elastic side panels 34 each have a longitudinal outer edge, a leg end edge 70 disposed toward the longitudinal center of the diaper 20, and waist end edges 72 disposed toward a longitudinal end of the absorbent article. The leg end edges 70 of the absorbent article 20 may be suitably curved and/or angled relative to the lateral direction to provide a better fit around the wearer's legs. However, it is understood that only one of the leg end edges 70 may be curved or angled, such as the leg end edge of the back region 24, or alternatively, neither of the leg end edges may be curved or angled, without departing from the scope of the present disclosure.

The fastening system 80 may include laterally opposite first fastening components 82 adapted for refastenable engagement to corresponding second fastening components 84. In the embodiment shown in the figures, the first fastening component 82 is located on the elastic side panels 34, while the second fastening component 84 is located on the front region 22 of the chassis 32. In one aspect, a front or outer surface of each of the fastening components 82, 84 includes a plurality of engaging elements. The engaging elements of the first fastening components 82 are adapted to repeatedly engage and disengage corresponding engaging elements of the second fastening components 84 to releasably secure the article 20 in its three-dimensional configuration.

In addition to possibly having elastic side panels, the absorbent article 20 may include various waist elastic members for providing elasticity around the waist opening. For example, as shown in the figures, the absorbent article 20 can include a front waist elastic member 54 and/or a back waist elastic member 56.

As described above, the present disclosure is particularly directed to incorporating a wetness indicating system into the absorbent article 20. In this regard, as shown in FIGS. 1-3, the absorbent article 20 includes a first conductive element 100 spaced from a second conductive element 102. In this embodiment, the conductive elements extend from the front region 22 of the absorbent article to the back region 24 without intersecting. The conductive elements 100 and 102 can comprise any suitable conductive metallic material, such as a conductive thread or a conductive foil. The first conductive element 100 does not intersect the second conductive element 102 in order to form an open circuit that may be closed, for instance, when a conductive fluid is positioned in between the conductive elements. In other embodiments, however, the first conductive element 100 and the second conductive element 102 may be connected to a sensor within the chassis. The sensor may be used to sense changes in temperature or may be used to sense the presence of a particular substance, such as a metabolite.

In the embodiment shown in FIG. 1, the conductive elements 100 and 102 extend the entire length of the absorbent article 20. It should be understood, however, that in other embodiments the conductive elements may extend only to the crotch region 26 or may extend to any particular place in the absorbent article where a body fluid is intended to be sensed.

The conductive elements 100 and 102 may be incorporated into the chassis 32 at any suitable location as long as the conductive elements are positioned so as to contact a body fluid that is absorbed by the absorbent article 20. In this regard, the conductive elements 100 and 102 generally lie inside the outer cover 40.

In order for the conductive elements 100 and 102 to be connected to a signaling device, the first conductive element 100 is attached to a first conductive pad member 104, while the second conductive element 102 is connected to a second conductive pad member 106. The pad members 104 and 106 are provided for making a reliable connection between the open circuit formed by the conductive elements to a signaling device that is intended to be installed on the chassis by the consumer. In particular, the pad members 104 and 106 create a target zone for attaching the signaling device and the conductive leads or elements.

Referring to FIG. 3, for exemplary purposes, a signaling device 110 is shown attached to the conductive pad members 104 and 106. As shown, in this embodiment, the signaling device generally 110 includes a transmitter 112 and a receiver 114. The transmitter 112 includes a pair of opposing terminals that are electrically connected to the corresponding conductive pad members. When a body fluid is present in the absorbent article 20, the open circuit formed by the conductive elements 100 and 102 is closed which, in turn, activates the signaling device 110. In particular, in this embodiment, the transmitter 112 sends a wireless signal to the receiver 114 which then indicates to a user that a body fluid is present in the absorbent article.

The signaling device 110 can emit an audible signal or a visual signal in order to indicate to the user that the circuit has been closed. The audible signal, for instance, may be as simple as one or more beeps to perhaps emitting a musical tune. Similarly, if the signaling device 110 issues a visible signal, the visible signal may comprise a few lights or an interactive display. In still another embodiment, the receiver 114 of the signaling device 110 may be configured to vibrate when the circuit within the absorbent article is closed.

As described above, the signaling device 110 can be configured to indicate the presence of any suitable conductive fluid within the absorbent article 20. The fluid may comprise, for instance, urine, a metabolite, and the like.

In the embodiment shown in FIG. 3, the signaling device 110 includes a transmitter 112 in combination with a receiver 114. It should also be understood, however, that the signaling device may comprise a single unit that remains attached to the absorbent article 20. For example, the signaling device may be mounted on the absorbent article and issue a visible signal and/or an audible signal from the article itself.

Absorbent articles, such as the absorbent article 20 as shown in FIG. 1, are typically made in process lines at very fast rates. Incorporating conductive elements into the absorbent articles at such fast speeds can be problematic. In this regard, the present disclosure in one embodiment, is directed to a process for quickly checking the quality of the produced products. In particular, the process can be used to assist in verifying that the absorbent articles are made with a wetness sensing system.

Figure 4:
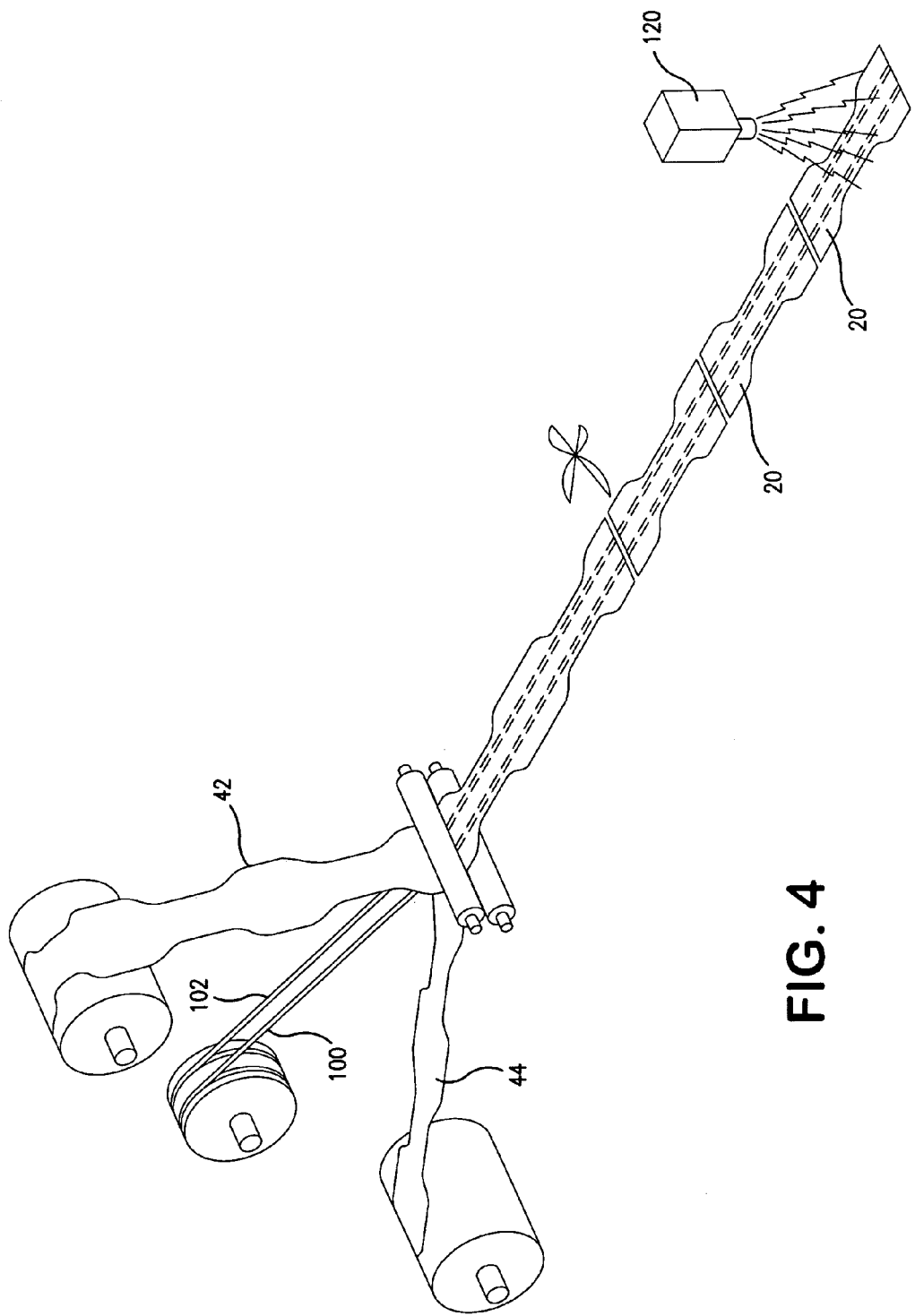
FIG. 4 is one embodiment of a process for producing absorbent articles in accordance with the present disclosure.

For instance, referring to FIG. 4, a simplified process diagram is shown for producing the absorbent articles 20. In this regard, it should be understood that a commercial absorbent article production line is relatively complicated with a significant number of moving equipment that constantly provides certain parts to the article as it is produced. Thus, the illustration provided by FIG. 4 is for exemplary purposes only.

As shown in FIG. 4, a bodyside liner 42 in combination with an absorbent structure are fed into a process line with an outer cover 44. In addition, conductive elements 100 and 102 are also fed into the process in order to form at least a portion of a wetness sensing system. In this embodiment, the conductive elements 100 and 102 are positioned in between the outer cover 44 and the bodyside liner 42. Once the materials are laminated together, a cutting step takes place in order to form the absorbent articles 20.

In accordance with the present disclosure, in order to verify that the absorbent articles contain a wetness sensing system, the absorbent articles are passed in close proximity to a metal sensor 120. Metal sensor 120 is configured to detect the presence of a metallic material that is used to produce the conductive elements 100 and 102 thereby confirming that an open circuit is present in the absorbent article 20.

In general, any suitable metal sensor may be incorporated into the process of the present disclosure. The particular metal sensor selected, for instance, may depend upon the type of material used to construct the conductive elements 100 and 102 and the amount of sensitivity that is desired for the application.

For example, in one embodiment, the metal sensor 120 may comprise an induction balance metal detector which typically operates at relatively low frequencies such as from about 30 kHz to about 300 kHz. Such metal detectors typically include a transmitter and a receiver. The transmitter may include a transmit coil. An electric current may be driven through the coil to create an electromagnetic field. Further, the flow of the current is reversed over and over again in a very rapid manner. The number of times the current is reversed over a period of time produces the operating frequency of the device.

As the current is reversed within the coil, the polarity of the magnetic field that is produced changes. When the magnetic field is placed in close proximity to a metallic object, the object causes a disturbance in the magnetic field and, in fact, can produce its own magnetic field.

The metal detector further includes a receiver placed in proximity to the transmitter. The receiver, for instance, may also comprise a coil of wire. The transmitter is configured so that a field produced by the currents flowing in a conductive object that come in close proximity to the metal sensor will cause currents to flow in the receive coil. These currents can then be amplified and processed by a microprocessor.

The signal received in the receiver and caused by a conductive object is typically delayed in comparison to the transmitted signal. This delay is due to the tendency of conductors to impede the flow of current and to impede the changes in the flow of current. This delay is often referred to a "phase shift". For metal objects which are primarily inductive, a large phase shift will incur. Inductive objects can be large objects or objects made from good conductors such as silver, gold and copper. Smaller objects or objects made from less conductive materials, on the other hand, typically display a smaller phase shift.

In addition to induction balance metal detectors, the metal sensor may also comprise a pulse induction metal detector. In a pulse induction metal detector, a single coil of wire is commonly used for both the transmitter and the receiver. A current is fed through the coil of wire and pulses. The pulses can range at a frequency from about 20 pulses per second to over 3,000 pulses per second. In these types of metal detectors, a pulsating magnetic field is produced. When a conductive object is placed near the device, the object interferes with the electromagnetic field and increases the time it takes for the pulse to decay to zero. The change in the width of the reflected pulse is measured to signal the presence of an object.

In addition to the above, it should be understood that various other metal sensors may be used. For instance, a metal detector having a three coil system in order to detect small particles of non-ferrous and stainless steel may also be used. Metal sensors can be obtained from various commercial sources including Advanced Detection Systems of Milwaukee, Wis., Mettler Toledo of Ithaca, N.Y., Cintx of America of Kenosha, Wis., Loma International of Carol Stream, Ill., EG&G. Astrophysics Inspection Systems of Long Beach, Calif., Safeline Metal Detection of Tampa, Fla., and the like.

The metal sensor 120 as shown in FIG. 4, can be configured to provide various information about the absorbent articles 20 depending upon the particular application. For example, in one embodiment, the metal sensor 120 may be used simply to confirm that a metallic material is present within the absorbent article. In this embodiment, for instance, the metal sensor 120 may produce a signal, such as an audible or visual signal, when the absorbent article contains a metallic material or, alternatively, when an absorbent article does not contain a metallic material.

In other embodiments, however, more sophisticated sensors may be used. For instance, in an alternative embodiment, the metal sensor may be configured to detect whether or not a metallic material is present in the absorbent article 20 within a pre-selected range. Thus, should the absorbent article contain too little metallic material and/or contain too much metallic material, a signal may be generated indicating a possible manufacturing flaw.

The metal sensor 120 can also be configured and/or programmed to not only sense a pre-selected amount of metallic material, but can also be configured to only sense certain types of materials. For example, metal sensors are capable of discerning between various different conductive materials. For instance, in one embodiment, the metal sensor 120 may be capable of discerning between ferrous materials and non-ferrous materials. In other embodiments, the metal sensor 120 may also be configured to discriminate between different types of metals, such as iron, steel, gold, nickel, copper, zinc, brass and silver. Depending upon the type of metallic material used to produce the conductive elements 100 and 102, the metal sensor 120 may be configured so as to only detect that particular type of material.

Having a metal sensor with selectivity as described above is typically referred to as the process of using "discrimination". Thus, the metal sensor 120 can be configured to only detect certain types of metallic materials and can also be configured so as to detect those particular types of metallic materials within particular ranges. In one particular embodiment, for instance, ferrous materials may be used to produce the conductive elements 100 and 102. In this embodiment, if desired, the metal sensor 120 can be configured to only sense ferrous materials.

The amount of metallic material incorporated into the absorbent article 20 can vary dramatically depending upon various factors. For exemplary purposes only, in one particular embodiment, the absorbent article may contain a metallic material in the amount from about 0.05 grams to about 1 gram per article. The metallic material may comprise a ferrous metal or a non-ferrous metal. In one embodiment, for instance, the metallic material comprises aluminum. As described above, a metal sensor can be used that is sensitive enough to indicate when the amount of metallic material contained within the article is above or below the above range.

In still another embodiment, the metal sensor can be configured not only to scan for a particular material used to construct the wetness sensing system, but can also simultaneously scan for other materials to determine whether any unwanted metallic materials have been incorporated into the product or the packaging for the product. For example, in one embodiment, the metal sensor can comprise a metal detector having multiple cores that scan for ferrous and non-ferrous metals. In this arrangement, it is possible to scan for an acceptable range of one particular metal, such as aluminum, and still scan for unwanted materials, such as ferrous and non-ferrous metals. Thus, in this embodiment, the metal sensor is not only used to verify the presence of the wetness sensing system but is also used to scan for any unwanted materials that may have been included in the product or the packaging for the product.

In addition to a wetness sensing system, it should be understood that the process of the present disclosure can also be used to verify the presence of other components. For instance, it has been proposed in the past to incorporate into absorbent articles or into the packaging of absorbent articles RFID devices. Such devices may contain a metallic material. If desired, the process of the present disclosure can also be used to verify the presence of RFID devices.

In the embodiment illustrated in FIG. 4, the absorbent articles 20 are passed below the metal sensor 120 during production of the articles. According to the present disclosure, however, the articles can be checked at other times during the packaging, sale and use of the articles. For example, in one embodiment, it may be desirable to conduct a quality control test on the articles after the articles have been packaged. For example, referring to FIG. 5, a package 122 of absorbent articles 20 is illustrated. In this embodiment, each of the absorbent articles 20 includes a wetness sensing system. The wetness sensing system, for instance, may include a pair of metallic conductive elements 100 and 102. The absorbent articles 20, in this embodiment, are enclosed within a shrink wrapped package. It should be understood, however, that the process of the present disclosure can be carried out on any suitable type of package.

In accordance with the present disclosure, the package 122 is placed in proximity to a metal sensor 120. In this embodiment, the metal sensor 120 is configured to be held by a user and scanned over the package. Alternative, such as shown in FIG. 4, the metal sensor 120 may be positioned at a fixed location and the package 122 may be conveyed, such as on a conveyor, in close proximity to the detector.

Figure 5:
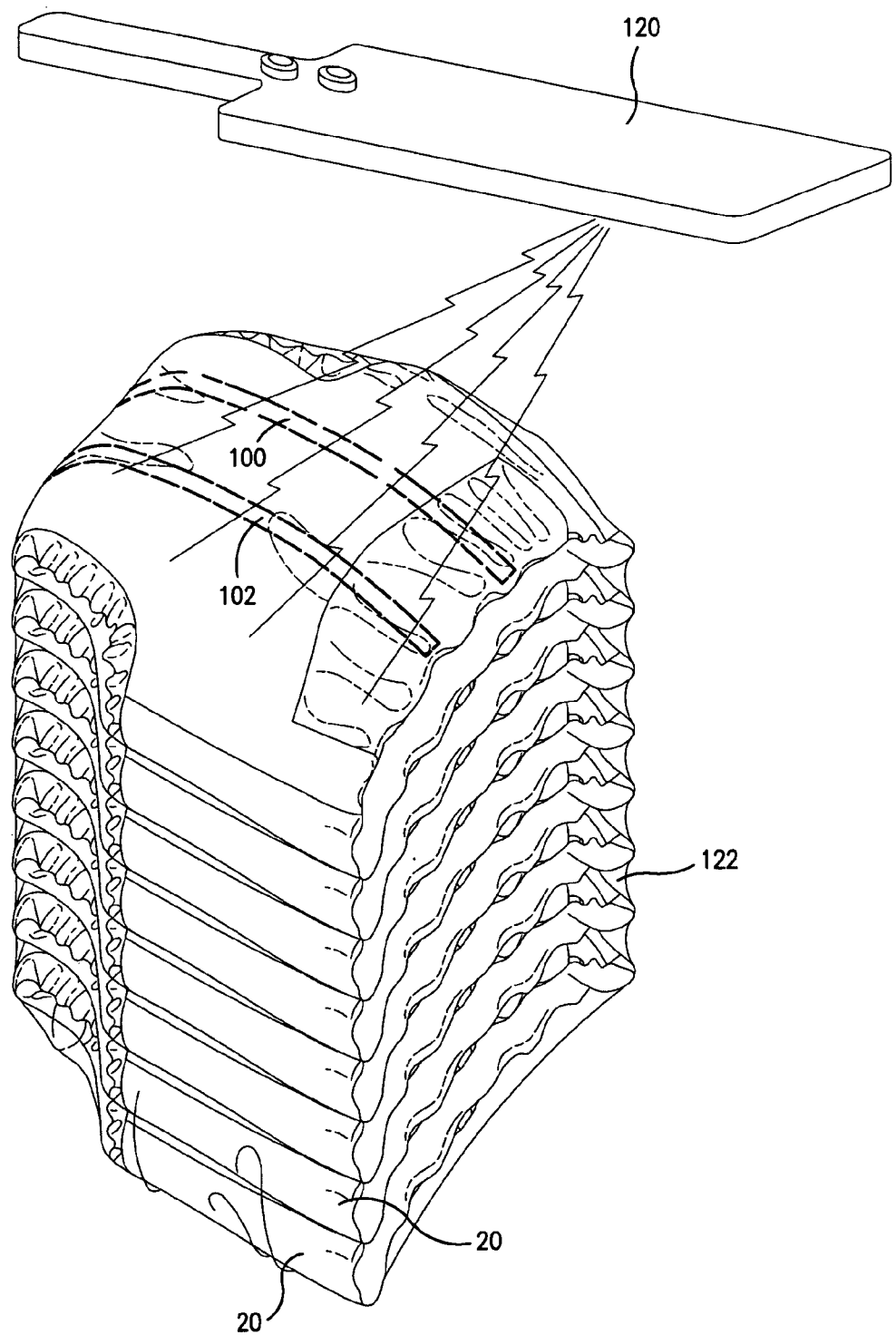
FIG. 5 is a perspective view of another embodiment of a process in accordance with the present disclosure for determining the presence of a wetness sensing system within a package of absorbent articles.

As shown in FIG. 5, the metal sensor 120 is passed over the package 122 in order to confirm the presence of wetness sensing systems within the individual absorbent articles. In particular, the package 122 may be placed in proximity to the metal sensor 120 so that the metal sensor can detect whether the package contains sufficient amount of metallic material that confirm that each absorbent article in the package contains a wetness sensing system. In one particular embodiment, for example, the metal sensor 120 can be configured to generate a signal when the package 122 contains the metallic material in an amount outside of a pre-selected range. For instance, the metal sensor may release an audible signal or a visual signal when the package contains more metallic material than it should and/or less metallic material than it should. In alternative embodiment, instead of releasing an audible or visual signal, the metal detector may release some other type of electric signal that then removes the package 122 from a conveyor line and places it in a bin designed to hold defective product.

When the metal sensor 120 is configured to detect a metallic material in an amount within a pre-selected range within the package 122, the pre-selected range can be calculated by determining how much metallic material should be in each absorbent article and then multiplying that amount times the number of articles in the package. A range can be also calculated that allows for some tolerance and non-uniformities in each article. This information can then be programmed into the metal sensor during operation of the quality control process. In fact, in one embodiment, a metal sensor 120 can be selected that is adjustable so that the metal sensor can be used to detect metallic materials and packages containing different amounts of absorbent articles and/or packages containing smaller or larger absorbent articles or absorbent articles containing different types of wetness sensing systems.

In the process illustrated in FIG. 5, in one embodiment, the package 122 can be scanned by the metal sensor 120 at the location at which the package is formed. Alternatively, the process may also be carried out at a wholesale or retail location prior to entering the package into inventory.

Figure 6:
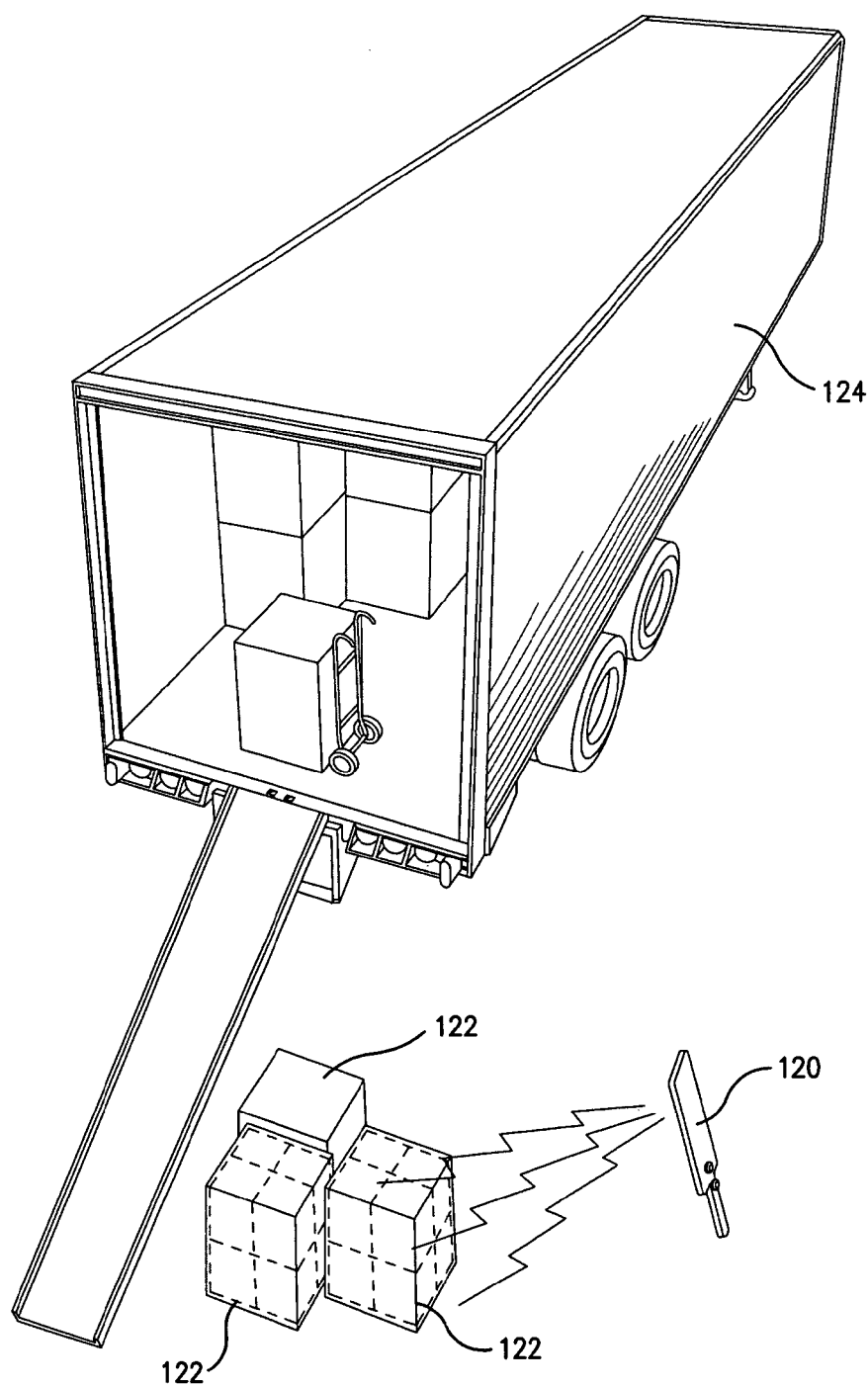
FIG. 6 is still another embodiment of a process in accordance with the present disclosure for confirming the presence of wetness sensing systems within packaged absorbent articles.

For example, referring to FIG. 6, another embodiment of a process in accordance of the present disclosure is illustrated. In this embodiment, packages 122 of absorbent articles are shown being unloaded from a trailer 124. As the packages 122 are unloaded from the trailer, the packages are placed in proximity to a metal sensor 120 which can be used to confirm the presence of wetness sensing systems contained within the packaged absorbent articles.

In the embodiment shown in FIG. 6, the packages can be scanned in order to verify their contents and can also be used to ensure that the absorbent articles are properly manufactured. If a package is found acceptable, the package can then be placed in inventory for retail sale. A defective package, on the other hand, may be reloaded on the truck 124 and returned to the manufacturer for closer inspection.

In still another embodiment of the present disclosure, the quality control process may be carried out by the ultimate purchaser of the product such as at the point of sale. For example, in FIG. 7, a plurality of packages 122 are shown on a shelf within a retail store. Affixed to a shelf is a metal sensor 120 that is provided for consumer use. In this embodiment, a consumer may select one of the packages 122 and scan the package with the metal sensor 120 in order to ensure that the articles contained within the package have been manufactured incorporating a wetness sensing system. In this manner, consumer confidence in the product greatly increases.

In one embodiment, the packages 122 may include graphics applied to an exterior surface. The graphics may include instructions 130 that provide basic steps and directions on how to use the metal sensor 120 in order to confirm the presence of the wetness sensing system. The instructions, for instance, may inform a consumer as to the distance at which the package should be separated from the metal sensor 120 and the distance at which the package should be separated from the remainder of the packages. The instructions may also provide other helpful tips on how to operate the metal sensor 120. For instance, the metal sensor 120 may have to be adjusted depending upon the package that is being scanned. For example, in one embodiment, the metal sensor 120 may include controls, such as a dial, that can be set depending upon the package being scanned. For instance, a consumer may be asked to input into the metal sensor 120 the number of absorbent articles in the package that is scanned. From this input, the metal sensor 120 can determine the amount of metallic material to sense for.

In the embodiment illustrated in FIG. 7, the instructions 130 are applied directly to the packages 122. It should be understood, however, that the instructions can be displayed at other locations. For instance, in an alternative embodiment, the instructions may be placed on the metal sensor 120. In still another embodiment, the instructions can be on a sign that is placed adjacent to the metal sensor 120.

By allowing a consumer to scan the package prior to purchase, the consumer can develop a substantial amount of confidence in the quality of the product. It should be understood, however, that the consumer can scan a package or a single article at other locations. For instance, if desired, a consumer may scan an absorbent article as it is unloaded from the package or after the article has been placed on a child.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. A process for producing and controlling the package quality of manufactured absorbent articles comprising:
   incorporating into an absorbent article a wetness sensing system that is configured to detect the presence of a substance, the wetness sensing system comprising at least one metallic conductive element;
   packaging together a plurality of the absorbent articles each incorporating a wetness sensing system; and
   passing the absorbent articles in proximity to a metal sensor, the metal sensor detecting the presence of the wetness sensing system in order to confirm that the wetness sensing system has been incorporated into the articles, the metal sensor being configured to indicate whether the package contains sufficient metallic material that confirms each absorbent article in the package contains a wetness sensing system.

2. The process as defined in claim 1, wherein the metal sensor operates by creating an electromagnetic field.

3. The process as defined in claim 1, wherein the package is passed in proximity to the metal sensor prior to being shipped from a location where the absorbent articles are packaged together.

4. The process as defined in claim 1, wherein the package is passed in proximity to the metal sensor as the package is added to inventory at a wholesale or retail location.

5. The process as defined in claim 1, wherein the package is passed in proximity to the metal sensor at a point of sale of the package to the consumer.

6. The process as defined in claim 1, wherein the absorbent article is passed in proximity to the metal sensor after the article has been sold to a consumer.

7. A process for producing and controlling the packaging quality of manufactured absorbent articles comprising:
   producing absorbent articles incorporating a wetness sensing system, the wetness sensing system being configured to detect the presence of a substance in the absorbent article, the wetness sensing system comprising at least one metallic conductive element;
   loading a plurality of the absorbing articles into a package; and
   passing the package in proximity to a metal sensor, the metal sensor being configured to detect whether the package contains sufficient amounts of a metallic material that confirms that each absorbent article in the package contains a wetness sensing system.

8. The process as defined in claim 7, wherein the package is passed in proximity to the metal sensor prior to being shipped from a location where the absorbent articles are packaged together.

9. The process as defined in claim 7, wherein the package is passed in proximity to the metal sensor as the package is added to inventory at a wholesale or retail location.

10. The process as defined in claim 7, wherein the package is passed in proximity to the metal sensor at a point of sale of the package to a consumer.

11. The process as defined in claim 7, wherein the metallic sensor is configured to generate a signal when a package contains the metallic material in an amount outside of a preselected range, thus indicating that the package contains more or less metallic material than desired.

12. The process as defined in claim 11, wherein the signal is audible or visual.

13. The process as defined in claim 11, wherein the preselected range is from about 0.05 grams per absorbent article times the number of absorbent articles in the package to about 1 gram per absorbent article times the number of absorbent articles in the package.

14. The process as defined in claim 7, wherein the metal sensor is held by a user and scanned over the package.

15. The process as defined in claim 7, wherein the metal sensor is positioned at a fixed location and wherein the package is passed in proximity to the metal sensor by being conveyed through the fixed location.

16. The process as defined in claim 7, wherein the metallic material detected by the metal sensor comprises a ferrous material and wherein the metal sensor is configured only to detect ferrous metals.

17. The process as defined in claim 7, wherein the metallic material detected by the metal sensor comprises a non-ferrous material and wherein the metal sensor is configured only to detect non-ferrous metals.

18. The process as defined in claim 7, wherein the wetness sensing system includes a first metallic material and wherein the metal sensor is configured to detect the presence of the first metallic material, the metal sensor also being configured to independently detect the presence of other metallic materials for confirming that the package does not contain such other metallic materials.

19. The process as defined in claim 7, wherein the metal sensor comprises an induction balance metal detector that operates at a frequency from about 30 kHz to about 300 kHz.

20. The process as defined in claim 7, wherein the metal sensor comprises a pulse induction metal detector.

21. A package of absorbent articles comprising:
    a plurality of absorbent articles, at least certain of the absorbent articles containing a wetness sensing system, the wetness sensing system comprising at least one metallic conductive element;
    a package housing enclosing the absorbent articles, the packaging housing having an interior surface and an exterior surface; and
    graphics including instructions directed to placing the package into proximity with a metal sensor for confirming the presence of the wetness sensing system present in at least certain of the absorbent articles.

22. The package as defined in claim 21, wherein the absorbent articles comprise diapers.

23. The package as defined in claim 21, wherein each of the absorbent articles includes an outer cover, a bodyside liner, and an absorbent structure positioned between the outer cover and the bodyside liner.

24. The package of absorbent articles as defined in claim 21, wherein the graphics are applied to the exterior surface of the package housing.

25. A process for producing and controlling the package quality of manufactured absorbent articles comprising:
    incorporating into an absorbent article a wetness sensing system that is configured to detect the presence of a substance, the wetness sensing system comprising at least one metallic conductive element; and
    passing the absorbent article in proximity to a metal sensor, the metal sensor detecting the presence of the wetness sensing system in order to confirm that the wetness sensing system has been incorporated into the article, the metal sensor being configured to indicate whether each absorbent article contains metallic material within a selected range and is configured to signal when the amount of metallic material contained within the absorbent article is outside of the selected range.

* * * * *

UNITED STATES PATENT AND TRADEMARK OFFICE
CERTIFICATE OF CORRECTION

| | |
|---|---|
| PATENT NO. | : 7,659,815 B2 |
| APPLICATION NO. | : 11/513832 |
| DATED | : February 9, 2010 |
| INVENTOR(S) | : Cohen et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 787 days.

Page 1 of 1

Signed and Sealed this

Thirtieth Day of November, 2010

David J. Kappos
*Director of the United States Patent and Trademark Office*